United States Patent [19]

Caudillo et al.

[11] Patent Number: 5,443,502
[45] Date of Patent: Aug. 22, 1995

[54] ROTATABLE HEART VALVE HOLDER

[75] Inventors: Roberto Caudillo; Rebecca Scoggins, both of Austin, Tex.

[73] Assignee: Carbomedics, Inc., Austin, Tex.

[21] Appl. No.: 253,097

[22] Filed: Jun. 2, 1994

[51] Int. Cl.⁶ .......................... A61F 2/24; A61M 1/00
[52] U.S. Cl. ......................................... 623/2; 623/900; 606/1
[58] Field of Search ................... 623/2, 900; 606/1

[56] References Cited

U.S. PATENT DOCUMENTS

| | | | |
|---|---|---|---|
| 3,860,005 | 1/1975 | Anderson et al. | 128/303 |
| 4,065,816 | 1/1978 | Sawyer | 623/2 |
| 4,182,446 | 1/1980 | Penny | 206/205 |
| 4,185,636 | 1/1980 | Gabbay et al. | 606/148 |
| 4,197,593 | 4/1980 | Kaster et al. | 623/2 |
| 4,211,325 | 7/1980 | Wright | 206/438 |
| 4,585,453 | 4/1986 | Martin et al. | 623/2 |
| 4,655,218 | 4/1987 | Kulik et al. | 128/321 |
| 4,679,556 | 7/1987 | Lubock et al. | 606/1 |
| 4,683,883 | 8/1987 | Martin | 623/2 |
| 4,702,250 | 10/1987 | Ovil et al. | 623/2 |
| 4,755,181 | 7/1988 | Igoe | 606/1 |
| 4,865,600 | 10/1989 | Carpentier et al. | 623/900 |
| 4,878,494 | 11/1989 | Phillips et al. | 128/334 R |
| 4,932,965 | 6/1990 | Phillips | 606/1 |
| 5,011,481 | 4/1991 | Myers et al. | 623/2 |
| 5,041,130 | 8/1991 | Cosgrove et al. | 623/2 |
| 5,071,431 | 12/1991 | Sauter et al. | 623/2 |
| 5,163,955 | 11/1992 | Love et al. | 623/2 |
| 5,197,979 | 3/1993 | Quintero et al. | 623/2 |
| 5,236,450 | 8/1993 | Scott | 623/2 |

FOREIGN PATENT DOCUMENTS

| | | | |
|---|---|---|---|
| 0809965 | 4/1969 | Canada | 623/2 |
| 1690738 | 11/1991 | U.S.S.R. | 623/2 |

Primary Examiner—David H. willse
Assistant Examiner—Bruce E. Snow
Attorney, Agent, or Firm—John R. Merkling

[57] ABSTRACT

A hinged heart valve holder and suturing method whereby the heart valve holder can be secured within a mechanical heart using a single suture. This suture operates both to secure the hinged heart valve holder within the annulus of the heart valve and to prevent the sewing ring from rotating on the annular valve body. Severing the suture at a single point both releases the heart valve holder and the sewing ring, permitting the annular valve body to be rotated within the sewing ring. Simultaneously, the suture remains secured to the heart valve holder and thus will be withdrawn in its entirety from the operation site.

9 Claims, 3 Drawing Sheets

ROTATABLE HEART VALVE HOLDER

FIELD OF OUR INVENTION

Our invention relates to mechanical prosthetic heart valves, and particularly to apparatus for holding such heart valves during surgical implantation in the heart of the patient.

BACKGROUND OF OUR INVENTION

Prosthetic heart valves fall generally into two categories: mechanical heart valves and bioprosthetic heart valves. Mechanical heart valves are conventionally constructed with a rigid annular body supporting one, two, or more leaflets. The action of these leaflets in opening and closing controls the flow of blood through the valve. The annular body of the heart valve is secured in a sewing ring, a structure which is usually comprised of Dacron (TM) or some other biocompatible material which permits a surgeon to stitch the valve into a location in the heart.

Holding the valve in position while implantation takes place has been and remains a problem for which new solutions are sought. One solution has been a holder for the heart valve which has two opposed substantially mirror-image halves which are joined by a pin or hinge. Adjacent to the heart valve, two jaws operate outwardly to engage the heart valve from the inside. This has been a generally satisfactory configuration in many instances.

Recently, however, mechanical prosthetic heart valves have been developed which have rotatable sewing rings. If a hinged valve holder is used with these valves, the sewing ring is still free to rotate during implantation. This adversely affects implantation.

SUMMARY OF OUR INVENTION

We have invented a hinged heart valve holder and suturing method whereby the heart valve holder can be secured within a mechanical heart valve using a single suture. This suture operates both to secure the hinged heart valve holder within the annulus of the heart valve and to prevent the sewing ring from rotating on the annular valve body. Severing the suture at a single point both releases the heart valve holder and the sewing ring, permitting the annular valve body to be rotated within the sewing ring. Simultaneously, the suture remains secured to the heart valve holder and thus will be withdrawn in its entirety from the operation site.

With the foregoing in mind, it is the object of our invention to provide a heart valve holder which can be secured to a mechanical heart valve having a rotatable suture ring by a single suture.

It is further an object of our invention to provide such a structure which can be removed from the heart valve by severing the suture at a single point.

Another important object of our invention is to provide such a heart valve holder which retains the suture on the heart valve holder for complete withdrawal from the patient's body.

These and further objects and advantages of our invention will be apparent from the following detailed description taken with reference to the accompanying drawings.

DETAILED DESCRIPTION OF OUR PREFERRED EMBODIMENT

Figure 1:
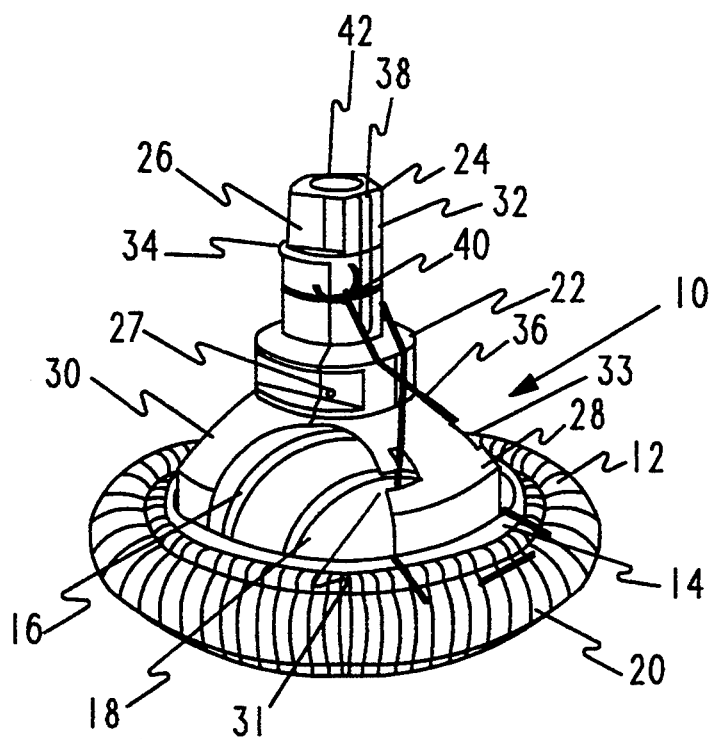
FIG. 1 is a perspective view of a mitral heart valve and hinged holder combination secured by a single suture, in accordance with our invention.
Figure 2:
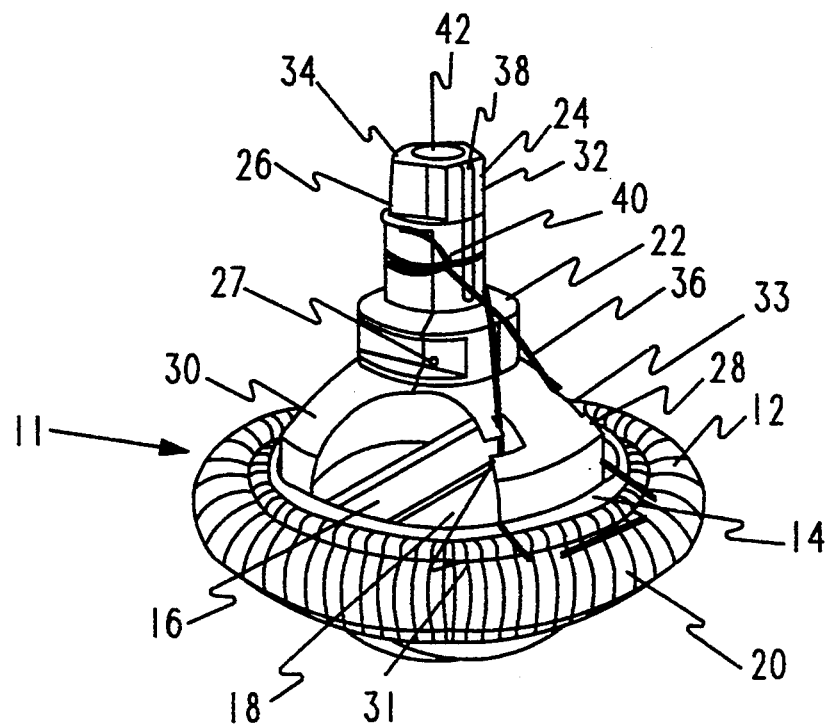
FIG. 2 is a perspective of an aortic heart valve with hinged holder sutured in accordance with our invention.

We will now describe our preferred embodiment with reference to the accompanying drawings. FIG. 1 illustrates a mitral mechanical prosthetic heart valve and holder combination generally designated 10. FIG. 2 illustrates an aortic mechanical heart valve and holder, generally designated 11. In all respects relevant to our invention, the mitral and aortic heart valves and holders are the same. A mechanical heart valve 12 comprises an annular valve body 14 which supports two pivoting leaflets 16, 18. These leaflets act to impede the flow of blood through the valve or to permit its flow out of the heart. Of course, mechanical heart valves with one or with more than two leaflets are also known. The annular valve body 14 is surrounded by a sewing ring 20. Sewing rings are well-known. Recently, sewing rings have been developed which permit the annular valve body 14 to rotate within the sewing ring. Such a sewing ring is described in U.S. Pat. No. 5,071,431 assigned to our Assignee. The reader is referred to that patent for further information related to this type of sewing ring.

Figure 9:
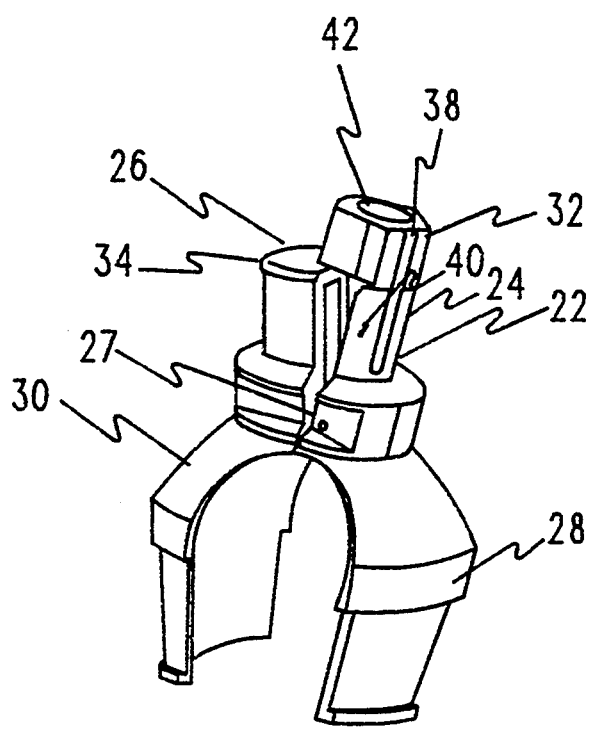
FIG. 9 is a perspective view of a prior art heart valve holder.

For implanting the heart valve, a valve holder 22 is used. The valve holder consists of two parts which are generally symmetrical to one another. For convenience we will designate a first part 24 as the front and a second part 26 as a back part. Such holders are also generally known and need not be described in detail. See, for example, FIG. 1 of U.S. Pat. No. 5,236,460. The prior art valve holder is illustrated in FIG. 9 in an opened condition with like numerals. However, our invention contemplates that the holder 22 would be hinged in some fashion, as, for example, by a pin 27. Two arms 28 and 30 are configured to press against an inside wall of the annular valve body 14. The arms 28 and 30 press outwardly against the valve body 14 when front and rear shafts parts, 32, 34 respectively, are held together. This is accomplished by a suture 36 as will be more particularly described below. In addition, suture 36 is secured to the sewing ring 20 and prevents the rotation of the valve body within the sewing ring or, alternatively, the rotation of the sewing ring with respect to the valve body during implantation of the mechanical heart valve. The front shaft part 32 also has a longitudinal cutting slot 38 which aids in cutting the suture 36. The front part 32 further has a transverse through bore 40, which is used in connection with the suture 36, as will be more particularly described below. A handle (not shown) is usually secured to the front shaft part 32 in a bore 42 in a conventional manner.

FIG. 2 is an additional perspective drawing of the features shown in FIG. 1, with the difference that the mechanical heart valve 12 is configured as an aortic heart valve, and the flow through the leaflets 16, 18 would be in the opposite direction from the flow through the valve shown in FIG. 1.

Figure 3:
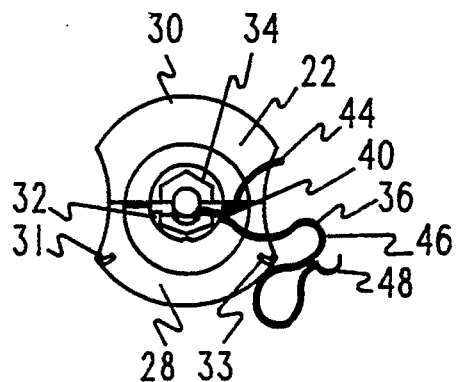
FIGS. 3 and 4 are top views of a heart valve holder showing two initial steps of securing the suture in accordance with our invention.
Figure 4:
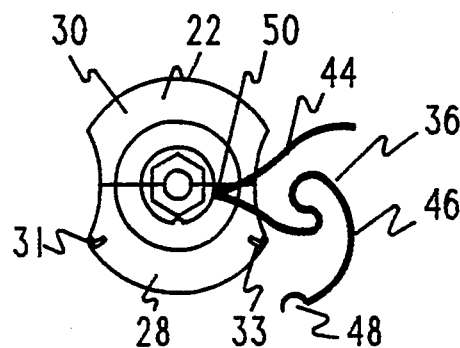
Figure 5:
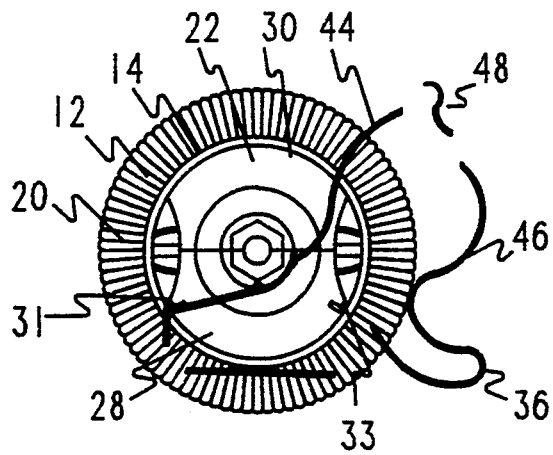
FIGS. 5 through 8 are top views of the heart valve holder and mitral mechanical heart valve of FIG. 1 showing additional steps in securing the suture in accordance with our invention.

Referring now to FIGS. 3 through 8, we will describe our method and apparatus for securing the valve holder and mechanical heart valve together with a single suture. FIG. 3 shows a top view of the valve holder 22 shown in FIG. 1, without the mechanical heart valve. The front shaft part 32 has been displaced in a direction which we will call "front" in accordance with our convention established heretofore (downward in FIG. 3), and slightly away from the back shaft part 34. This action operates to bring the arms 28, 30 slightly closer together, as would be necessary for inserting the valve holder into a heart valve, or removing the holder from the heart valve. The suture 36 is first passed through the transverse bore 40 with a short end 44 being brought back between the two shaft parts 32, 34 and a long end 46 extending out of the bore 40. The suture 36 should be provided with a suture needle 48. We prefer to use an integral suture and needle such as that available from Deknatel under the code 7-798. The short and long ends 44 and 46 of the suture 36 are tied together at a knot 50 outside the shaft part 32, as shown in FIG. 4. The holder 22 can still be opened and closed in this configuration. At this point, the holder 22 is inserted into the annular valve body 14 of the mechanical heart valve 12, as shown in FIG. 5. The long end 46 of the suture 36 is brought down toward the front of the holder 22 and across the holder. In the illustrated embodiment, the suture passes from the right side of the front shaft part towards a left side of the valve holder. The suture passes through an L-shaped slot in the arm 28. This tends to lock the suture formation in place around the valve holder. The suture is then passed close to the edge of the arm 28 to the sewing ring where it is stitched to the sewing ring by one or more stitches passing from left to right along the sewing ring. When these stitches have been made, the suture needle 48 is cut away from the long end of the suture, as also shown in FIG. 5.

Figure 6:
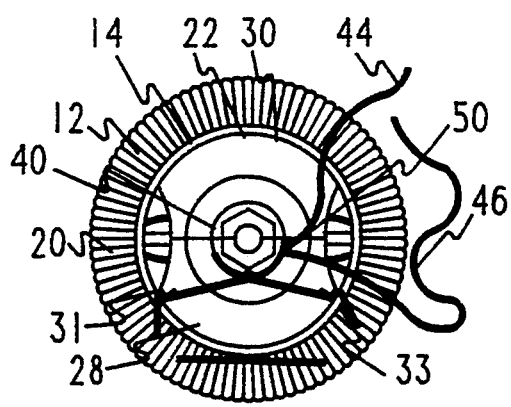
Figure 7:
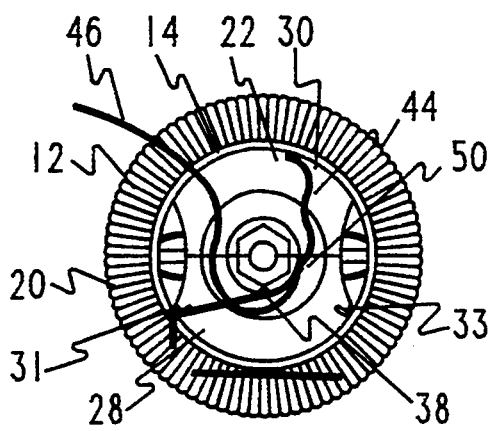
Figure 8:
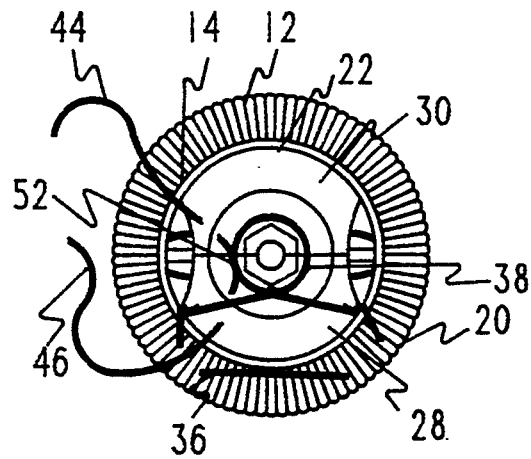

The suture is then lead back up and across the valve holder through another L-shaped slot 33 to the opposite side of front shaft part 32, forming a "figure eight", as shown in FIG. 6. The long part 46 of the suture 36 is then passed through the hole 40 so that it emerges from the shaft part adjacent the knot 50. The long end and the short end of the suture are then passed in opposite directions around the two shaft parts 32, 34, as shown in FIG. 7. The ends 44, 46 are tied together with a knot 52, preferably a double square knot, and the excess suture is cut away, as shown in FIG. 8.

This wrapping holds the two shaft parts together, thus preventing the arms 28 and 30 from closing and becoming disengaged from the annular valve body 14. At the same time, the suture prevents the sewing ring 20 from rotating around the valve body. As can be seen in FIG. 8, the suture passes immediately over the scalpel groove 38. By cutting the suture at this point only, a surgeon simultaneously releases the valve holder 22 and the suture ring 20. Nevertheless, the suture 36 remains secured to the valve holder 22 and the entire suture will be removed from the site of the operation with the valve holder.

We claim as our invention:

1. A combination comprising a mechanical heart valve and heart valve holder,
   said heart valve having
   a rigid annular valve body,
   at least one leaflet pivotally received in said rigid valve body for controlling the flow of blood therethrough, and
   a sewing ring circumferentially surrounding said valve body, said valve body being rotatable within said sewing ring, and
   said heart valve holder having
   a holding structure consisting of
   first arm means for selectively engaging said annular valve body,
   second arm means for selectively engaging said annular valve body, said second arm means being pivotally connected to said first arm means, and
   a front shaft part attached to said first arm means, said front shaft part having thereon means for engaging a handle.
   a back shaft part attached to said second arm means, said front and back shaft parts being configured such that when they are held adjacent each other said first and second arm means are forced against said annular valve body and
   a single suture having first and second ends,
   means for securing said first end of said suture to said holding structure, and
   means for securing said second end of said suture to said holding structure, said single suture acting to hold said front shaft part against said back shaft part and passing though said sewing ring, thereby securing said sewing ring against rotation, and permitting said holding structure, together with said single suture, to be removed from said heart valve when said suture has been severed at a single location between said first and second ends.

2. The combination according to claim 1 wherein at least one of said arm means further comprises a first slot through which said first end of said suture is passed and a second slot through which said second end of said suture is passed.

3. The combination according to claim 1 wherein the means for securing the first end of the suture comprise a bore in at least one of said shaft parts.

4. The combination according to claim 1 wherein the means for securing the second end of the suture comprise a bore in at least one of said shaft parts.

5. The combination according to claim 3 wherein the means for securing the second end of the suture comprise a bore in at least one of said shaft parts.

6. The combination according to claim 5 wherein the suture passes from the first end thereof to a position on the sewing ring spaced radially away from said first end in a first circumferential direction, stitches through said sewing ring toward said first end in a second circumferential direction opposite to said first direction, and passes from said sewing ring across the holding structure in said first direction to said second end.

7. The combination according to claim 6 wherein at least one of said arm means further comprises a first slot through which said first end of said suture is passed and a second slot through which said second end of said suture is passed.

8. The combination according to claim 6 wherein said second end passes through the bore in said shaft, circumscribes said shaft and is tied to the first end.

9. A method for securing a heart valve holder to a mechanical heart valve said heart valve having a rigid annular valve body, at least one leaflet pivotally received in said rigid valve body for controlling the flow of blood therethrough, and a sewing ring circumferentially surrounding said valve body, said valve body being rotatable within said sewing ring, and said heart valve holder having a first arm for engaging said annular valve body, a second arm for engaging said annular valve body, a first shaft part for engaging a handle and a second shaft part adjacent said first shaft part, said first shaft part being mounted on said first arm and said second shaft part being mounted on said second arm, said first and second arms being pivotally connected, and at least one of said shaft parts having a bore extending transversely therethrough, said method comprising the steps of securing a first end of a suture through said bore, inserting the arms of said valve holder in said heart valve, passing a second end of said suture from said first end to a first position on said sewing ring radially displaced from said first end in a first circumferential direction, stitching said suture through said sewing ring in a second circumferential direction opposite to said first direction to emerge at a second position on said sewing ring, passing said second end of said suture from said second position on said sewing ring to said bore in said first circumferential direction, threading said suture through said bore, wrapping said suture around both said first and said second shaft parts, and securing said second end of said suture to said first end.

\* \* \* \* \*